United States Patent [19]

Kozlowski, Jr.

[11] 4,157,758
[45] Jun. 12, 1979

[54] SURGICAL BLADE PACKAGE ASSEMBLY

[75] Inventor: George J. Kozlowski, Jr., Billerica, Mass.

[73] Assignee: Rudolph Beaver, Inc., Belmont, Mass.

[21] Appl. No.: 844,930

[22] Filed: Oct. 25, 1977

[51] Int. Cl.² .................. A61B 17/06; A61B 17/32; B65D 81/10

[52] U.S. Cl. .................. 206/363; 206/352; 206/438; 206/486

[58] Field of Search ............. 206/363, 352, 355, 356, 206/350, 486, 523, 524, 438, 382, 383, 336, 339

[56] References Cited

U.S. PATENT DOCUMENTS

| | | | |
|---|---|---|---|
| 3,481,462 | 12/1969 | Chapel | 206/438 |
| 3,530,213 | 9/1970 | Belle Isle | 206/523 |
| 3,819,039 | 6/1974 | Erickson | 206/486 |
| 3,944,069 | 3/1976 | Eldridge, Jr. | 206/350 |
| 3,970,194 | 7/1976 | Iten | 206/356 |
| 4,008,802 | 2/1977 | Freitag | 206/382 |

FOREIGN PATENT DOCUMENTS

| | | | |
|---|---|---|---|
| 1200204 | 9/1965 | Fed. Rep. of Germany | 206/523 |
| 2156933 | 2/1973 | Fed. Rep. of Germany | 206/355 |

*Primary Examiner*—Herbert F. Ross
*Attorney, Agent, or Firm*—Robert E. Ross

[57] ABSTRACT

A package assembly for a surgical blade comprising a U-shaped member formed of resilient material such as plastic foam and a surgical blade assembled into the foam between the legs forming the U-shaped member. The foam member protects the cutting edge of the blade during packaging and subsequent handling, and the legs of the U-shaped member may be easily bent to one side to allow grasping of the blade by a blade holder to remove it from the package for use.

5 Claims, 4 Drawing Figures

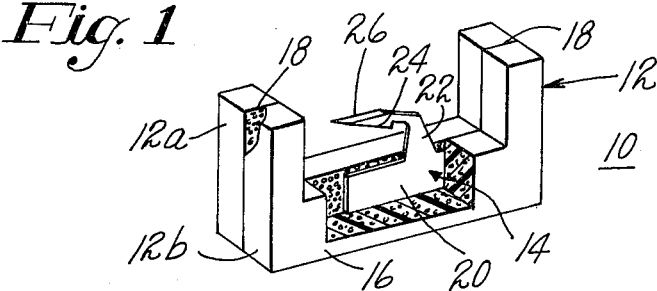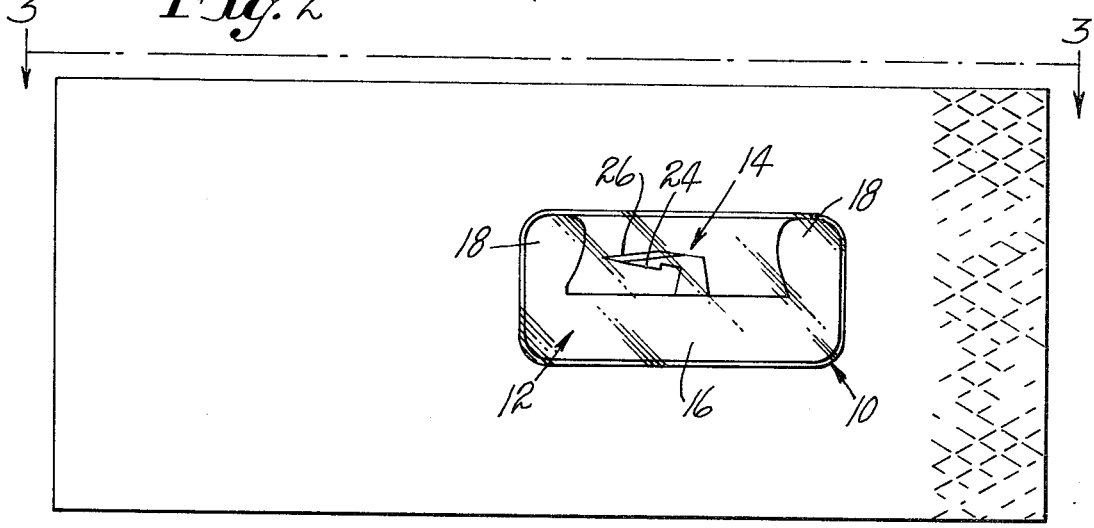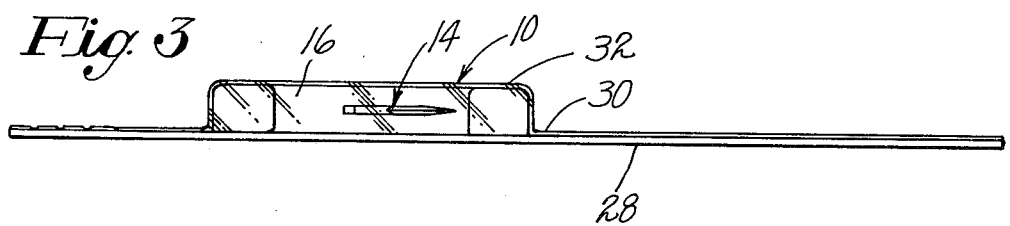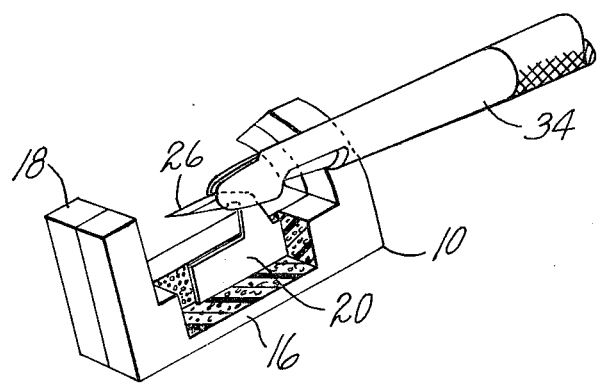

SURGICAL BLADE PACKAGE ASSEMBLY

BACKGROUND OF THE INVENTION

The manufacture of surgical blades of the type which are supplied in individual packages presents a problem in packaging, in that it is essential that the cutting edge not be touched after sharpening. However, the blades must be handled both by manufacturing personnel and the surgeon, and must be maintained in a sterile condition in the package.

SUMMARY OF THE INVENTION

This invention provides a surgical blade packaging assembly, in which a plastic foam structure retains a surgical blade, the foam being shaped to protect the cutting edge of the blade from being touched during normal handling of the package, yet allows easy removal of the blade by the surgeon by a so-called "blade breaker."

BRIEF DESCRIPTION OF THE DRAWINGS

FIG. 1 is a perspective view of a surgical blade package assembly embodying the features of the invention.

FIG. 2 is a top plan view of support onto which the assembly of FIG. 1 has been mounted.

FIG. 3 is a view taken on line 3—3 of FIG. 1.

FIG. 4 is a perspective view of the asembly of FIG. 1, illustrating the means of removing the blade from the assembly.

DESCRIPTION OF THE ILLUSTRATED EMBODIMENT

Referring to the drawing there is illustrated a surgical blade package assembly 10, which comprises a structure 12 formed of resilient material such as polyurethane foam, and a surgical blade 14 assembled therewith.

The structure 12 comprises a base portion 16 and a pair of upstanding legs 18 at the ends of the base. In a preferred embodiment of the invention, the structure 12 is formed of two portions 12a and 12b of similar shape, superimposed and held together by any convenient means such as adhesive.

The blade 14 may be of a type similar to that disclosed in a co-pending application Ser. 678,866 filed Apr. 21, 1976 by John R. Beaver and George J. Kozlowski and assigned to the same assignee as this application, and comprises a base portion 20, an upstanding tang portion 22, and a cutting portion 24 having a cutting edge 26 extending generally horizontally between the legs 18.

During assembly of the foam portions 12a and 12b, the blade may be positioned between the pieces when they are fastened together, so that thereafter the blade is securely retained in the foam structure. The dimensions of the foam and blade are such that the cutting portion 24 is disposed below the upper ends of the legs 18.

The package assembly 10 may be assembled onto a support card 28 and retained therein by a clear plastic blister-pack sheet 30 having a suitable pocket 32 enclosing the foam package 10. The card may be provided with information on the product and instructions for use (not shown).

In a commercial embodiment of the invention, the package may be sterilized after assembly in any well-known manner, such as by exposure to ethylene gas.

When the blade is to be used by the surgeon, after removal from the blister-pack, the foam package may be grasped at the base by one hand, and the tang 22 grasped with a "blade breaker" 34 which is a surgical tool normally used for grasping and breaking off shards of carbon steel or stainless steel razor blades for surgical use.

The fact that the legs 18 are formed of flexible material allows a leg to be easily bent aside to allow the blade breaker 34 to grasp the tang at the correct orientation.

By firmly holding the base 20 of the blade and slightly twisting the blade-breaker, the tang 22 will break away from the base 20. The structure of the blade breaker 34 is such that the blade is thereafter firmly held in the end thereof properly orientated for use in a surgical cutting procedure.

The foam structure surrounding the blade allows the assembly to be readily handled, or laid on a surface, without any danger of the cutting edge being touched before the blade is grasped by the blade breaker. The assembly, even if inadventently dropped onto a table or floor, will protect the cutting edge from damage.

Although in the illustrated embodiment the structure 12 is formed of two pieces of superimposed U-shaped plastic foam, it will be understood that other materials and other configurations could be used, provided that the blade is held securely therein, and is so shaped that the cutting edge of the blade is protected and provision is made for allowing the blade breaker to grasp the tang at the proper angle.

Since certain other obvious modifications may be made in the illustrated embodiment of the invention without departing from the scope thereof, it is intended that all matter contained herein be interpreted in an illustrative and not a limiting sense.

I claim:

1. A surgical blade package comprising a base, a surgical blade having a support portion retained in the base, said blade having a tang extending upwardly from the support portion and away from the base, a cutting portion disposed on the end of the tang, and a pair of resilient legs extending upwardly from opposite ends of the base forming an open area therebetween so that the cutting portion is disposed in said open area.

2. A surgical blade package comprising two pieces of material held together with a surgical blade retained therebetween, said blade having a base and cutting portion disposed above the base, and resilient means having spaced legs extending from the base and so positioned that the cutting portion of the blade is disposed between said legs and below the ends thereof.

3. A surgical blade package assembly comprising a blade holder formed of resilient material and comprising a base and spaced legs extending from the base in generallly the same direction forming an open area therebetween, and a surgical blade held by said holder, said blade having a support portion retained in the base portion of the blade holder, a tang portion extending therefrom and a cutting portion disposed on the tang portion, said cutting portion being disposed in said open area between the legs and below a line connecting the extreme ends of said legs.

4. A surgical blade package assembly comprising a blade holder formed of superimposed layers of resilient material having a base and upstanding legs disposed in spaced relation forming an open area therebetween, and a blade assembly therewith said blade having a portion retained between the layers of the base, a tang extending upwardly from said portion, and a cutting portion disposed on the tang and in the open area between the legs.

5. A package assembly as set out in claim 4 in which the blade holder is formed of resilient plastic foam.

* * * * *